United States Patent
Boenig et al.

(10) Patent No.: US 10,670,587 B2
(45) Date of Patent: Jun. 2, 2020

(54) ANTIBODY DETECTION METHOD AND SYSTEM

(71) Applicants: DRK-Blutspendedienst Baden-Wuerttemberg-Hessen gGmbH, Frankfurt am Main (DE); Johann Wolfgang Goethe-Universität Frankfurt am Main, Frankfurt am Main (DE)

(72) Inventors: Halvard Boenig, Frankfurt (DE); Christof Geisen, Cologne (DE); Eliza Justyna Wiercinska, Zwingenberg (DE); Nikolas Ryschka, Frankfurt am Main (DE)

(73) Assignees: DRK-Blutspendedienst Baden-Wuerttemberg-Hessen gGmgH, Frankfurt am Main (DE); Johann Wolfgang Goethe-Universitaet Frankfurt am Main, Frankfurt am Main (DE)

( * ) Notice: Subject to any disclaimer, the term of this patent is extended or adjusted under 35 U.S.C. 154(b) by 173 days.

(21) Appl. No.: 15/552,657

(22) PCT Filed: Feb. 25, 2016

(86) PCT No.: PCT/EP2016/053989
§ 371 (c)(1),
(2) Date: Aug. 22, 2017

(87) PCT Pub. No.: WO2016/135246
PCT Pub. Date: Sep. 1, 2016

(65) Prior Publication Data
US 2018/0340930 A1   Nov. 29, 2018

(30) Foreign Application Priority Data
Feb. 25, 2015  (EP) .................................. 15156590

(51) Int. Cl.
| | | |
|---|---|---|
| *G01N 33/53* | (2006.01) | |
| *G01N 33/80* | (2006.01) | |
| *C07K 16/34* | (2006.01) | |
| *G01N 33/50* | (2006.01) | |
| *B01D 15/38* | (2006.01) | |

(52) U.S. Cl.
CPC ......... *G01N 33/53* (2013.01); *B01D 15/3809* (2013.01); *C07K 16/34* (2013.01); *G01N 33/5094* (2013.01); *G01N 33/80* (2013.01); *C07K 2317/21* (2013.01)

(58) Field of Classification Search
None
See application file for complete search history.

(56) References Cited

U.S. PATENT DOCUMENTS

2007/0161056 A1   7/2007  Banerjee

OTHER PUBLICATIONS

Han et al. (Nature Biotechnology 2001 vol. 19, (Year: 2001).*
Suramanianet al. (Blood 2006 107: 2458-2556). (Year: 2006).*
Ward et al. (Veterinary Pathology 2014 51: 88-101) (Year: 2014).*
Bergmann-Leitneret al. (Malaria Journal 2008 7: 129 total 10 pages) (Year: 2008).*

* cited by examiner

*Primary Examiner* — Changhwa J Cheu
(74) *Attorney, Agent, or Firm* — Saliwanchik, Lloyd & Eisenschenk

(57) ABSTRACT

The present invention provides a cellular system for the detection of the presence of one or more antibody species in sample, preferably a serum or plasma sample. The method is in particular useful for the analysis of patients who have been sensitized against blood group antigens expressed on erythrocytes, platelets or granulocytes. The system uses fluorescence labeled cells specific for each antigen and hence, for each antibody species. Provided are the methods, system and diagnostic kits for performing the methods of the invention. In addition, the present invention discloses a method for removing antibodies from a sample such as a serum sample. Such a method is useful for absorbing antibodies from poly-agglutinating sera.

15 Claims, 4 Drawing Sheets

ANTIBODY DETECTION METHOD AND SYSTEM

CROSS REFERENCE TO A RELATED APPLICATION

Figure 1:
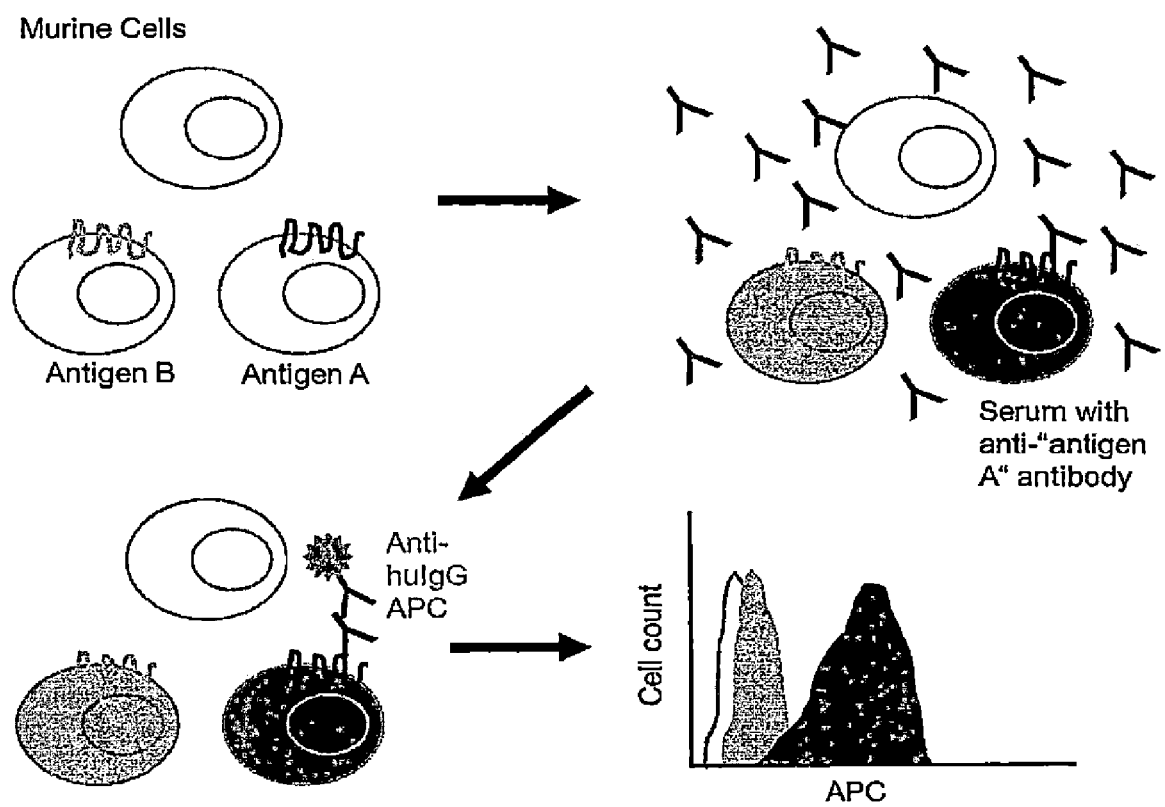

This application is a National Stage Application of International Application Number PCT/EP2016/053989, filed Feb. 25, 2016; which claims priority to European Patent Application No. 15156590.0, filed Feb. 25, 2015; both of which are incorporated herein by reference in their entirety.

FIELD OF THE INVENTION

The present invention provides a cellular system for the detection of the presence of one or more antibody species in sample, preferably a serum or plasma sample. The method is in particular useful for the analysis of patients who have been sensitized against blood group antigens expressed on erythrocytes, platelets or granulocytes. The system uses fluorescence labeled cells specific for each antigen and hence, for each antibody species. Provided are the methods, system and diagnostic kits for performing the methods of the invention. In addition, the present invention discloses a method for removing antibodies from a sample such as a serum sample. Such a method is useful for absorbing antibodies from poly-agglutinating sera.

DESCRIPTION

Secondary to sensitization (transfusion, pregnancy, etc.), antibodies against blood group antigens on erythrocytes (RBCs), platelets and granulocytes can be induced. As they may trigger adverse reactions in case of re-challenge, sensitive diagnostic tests are used for their detection.

Antigen-negative blood products are then used for transfusion. The detection of these antibodies hinges classically on the use of cell panels, each of which expresses the entire range of antigen specificities, albeit in random combination. Thereby, analyses of reaction strength with certain panel cells but not others is interpreted as reactivity against certain antigens (those that these individual panel cells share or have in common). Inversely, absence of reactivity with cells homozygously carrying a certain antigen is interpreted as non-reactivity with this antigen. There are today over 400 known RBC blood group antigens in 30 blood group systems and approximately a dozen granulocyte and platelet blood group antigens each. Being a natural cell (RBC, platelet or granulocyte from a donor), each panel cell obviously carries a host of antigens, typically at least one antigen from each group of antigens, or blood group system. For RBCS, tests for possible anti-RBC antigens are performed prior to every transfusion, of which there are more than 4 million per year in Germany alone. For granulocytes and platelets, transfusion of which is already significantly less frequent, because of lack of robust, rapid and affordable tests, antibody diagnostic is initiated only for patients with adverse reactions or refractoriness to transfusion.

In case of RBCs, many simple and highly effective routine tests are available, most of which hinging on panel reactivity as above-described. In some situations, these tests fail: When pan-agglutinating antibodies are present, no negative panel cells are present which could be used to rule out tolerance to certain antigens. In patients with auto-reactive antibodies, with a mix of antibodies against several antigens or with antibodies against high-frequency antigens, the tests similarly fail to allow identification of tolerable antigens. Thus antibody differentiation will be hampered or (combinations of) specific antibodies will be falsely interpreted as pan-agglutination, which typically is clinically irrelevant. Panels typically fail to identify antigens against rare antigens, because none of the cells in the panel will happen to express them; thus potentially serious antibodies may be missed. Thus standard diagnostics are available and most often yielding, but in specific situations fail. Some alternative tests exist, where blood group antigens are immobilized on fluorescent latex particles, but these are not suitable for the typical RBC antigens which are membrane proteins of very complex protein structure. By contrast, similar tests with platelets and granulocytes are less well standardized and significantly complicated by the short shelf life of platelet or granulocyte test panels.

In view of the aforementioned problems associated with state of the art blood group antigen antibody detection systems, the present invention seeks to provide an improved simpler methodology for determining blood groups in a sample from a subject.

In addition the present invention seeks to solve the problems associated with poly-agglutinating sera which contain antibodies against a multitude of blood group antigens. Such sera might be conducive to conventional diagnostics after selective removal of one or more antibody species. Thus, another problem the invention seeks to solve is to simplify removal or depletion of blood group antigen antibodies from a serum sample.

The above first problem is solved in a first aspect by a method for the detection of one or more antibody species in a sample, the method comprising
  a. Contacting a sample suspected to contain the one or more antibody species with one or more probing cell species and an antibody binding agent,
    i. wherein the antibody binding agent is coupled to a first detectable label and is capable of binding antibodies, and
    ii. wherein a probing cell of a probing cell species expresses, or is capable to express, a second detectable label and an antigenic protein, the antigenic protein comprising an antigenic portion that is capable of binding, or is capable to be bound by, an antibody of the one or more antibody species to be detected; and
  b. Detecting the presence of a signal from the first detectable label and the second detectable label for each probing cell, wherein the presence of a signal from the first detectable label and the presence of a signal from the second detectable label indicates the presence of the one or more antibody species in the sample.

The above first problem is solved in an alternative aspect by a method for the detection of one or more antibody species in a sample, the method comprising
  a. Contacting a sample suspected to contain the one or more antibody species with one or more probing cell species and an antibody binding agent,
    i. wherein the antibody binding agent is coupled to a first detectable label and is capable of binding antibodies, and
    ii. wherein a probing cell of a probing cell species is immobilized at a predetermined location on a solid substrate, and wherein the probing cell expresses, or is capable to express, an antigenic protein, the antigenic protein comprising an antigenic portion that is capable of binding, or is capable to be bound by, an antibody of the one or more antibody species to be detected; and b. Detecting the presence of a signal from the first detectable label for each probing cell immobilized on the solid substrate, wherein the presence of a signal from the first detectable label at a predetermined location on the solid substrate indicates the presence of the one or more antibody species in the sample.

In this aspect multiple probing cell species may be immobilized on one solid substrate at predetermined locations including positive and negative controls. The detection of the presence of the one or more antibody species in the sample is achieved by scanning the solid substrate for the signal of the first detectable label. Only the presence of the signal at the predetermined locations where a probing cell expressing the respective antigenic protein was immobilized is then indicative for the presence of the one or more antibody species in the sample.

The solid substrate or chip in this aspect may be a glass or plastic slide, or any other suitable carrier that allows for the immobilization of probing cell species. Detection of the one or more antibody species in the sample (for example for the detection of blood group antigen-specific antibodies) is achieved by using the antibody binding agent as described above. Suitable labels for the antibody binding agent will be described herein below. Identification of the presence or absence of the antibody species to be detected is in this embodiment based on the predetermined physical location of the probing cell species on the solid substrate (Chip) exactly in the same manner as if identification was by detection of the cell's fluorescent label and the second label on the anti-human Ig-antibody which must coincide to declare an antibody specificity.

The inventors here propose a novel method for blood group antigen detection on RBCs, platelets and granulocytes which is based on expression of only one antigen per cells (xenogeneic cell, any species, or human but not of the lineage of interest, i.e. not RBC, megakaryocyte/platelet or granulocyte lineage) and co-expressing one or several detectable markers. A mix of cells is prepared containing cells with surface expression of different antigens (all antigens of interest), each identified by a different fluorochrome. The cell mix is incubated with serum or plasma from the patient. Antibody against one of the cells is recognized by incubation of the cells in anti-human IgG conjugated to a discriminating fluorochrome not contained in the cell mix (e.g. APC). The cell mix is then analyzed by flow cytometry. The APC-positive (i.e. antibody-decorated) cell population is analyzed for its endogenous fluorescence, e.g. RFP. This indicates that the patient serum contained antibody against the single blood group antigen expressed by the RFP+ cell. Cell mixes will be generated containing cells together expressing groups of certain antigens, such as common antigens, rare antigens, high-frequency antigens, etc. to supplement the current armamentarium of RBC antibody diagnostics. Similarly, the cells expressing a common antigen obscuring diagnostics with standard technology can be depleted from sera. There for, patient serum containing, for instance, antibody against the antigen "e" from the Rh blood group system, a very frequent pseudo-specificity of autoreactive, clinically irrelevant but diagnostics-obscuring antibodies, is incubated with cells expressing, in this case, the blood group antigen "e". The cells will catch the antibody, be sedimented by centrifugation. The thusly anti-"e"-depleted serum can be subjected to routine diagnostics (detection of additional specific antibodies using standard or novel diagnostic tests). The same technology will be applied to express platelet or granulocyte antigens on cells, as described above, in order to detect with an anti-IgG-fluorochrome conjugated secondary antibody antibodies against HPA or HNA in patient sera. Even though less frequently required as a diagnostic test, it is expected that the much greater simplicity of this test compared to currently available technology will allow this test to become the routine diagnostic for anti-platelet and anti-granulocyte antibody.

By contacting the probing cell species and the antigen binding agent with the sample that is suspected to comprise one or more antibodies of the antibody species to be detected, in the event such an antibody is present, a complex of the probing cell species, the antibody to be detected and the antibody binding agent is formed. The complex is formed via the specific interaction of the antigenic protein in the probing cell and the complementary antibody to be detected, as well as the binding of the antibody binding agent to the antibody to be detected. Therefore, when observing the presence of the first and second (or more) detectable labels for one probing cell, the presence of both signals is indicative for the presence of the formed complex. In the event that the candidate antibody to be detected is not present, the complex is not formed, and no probing cell species has the first and the second detectable label.

The term "antibody binding agent" in context of the invention shall refer to any molecule having the capability to bind antibodies. In particular preferred are immunoglobulin proteins such as antibodies or TCR constructs. Most preferred for the herein disclosed matter is that the antibody binding agent is an antibody specific for the candidate antibody's organism type (species).

A "sample" in context of the present invention is preferably a biological sample. The term "biological sample" in context of the herein described invention preferably refers to a liquid sample such as a blood sample, serum sample, or plasma sample. As used hereinafter, the term "blood sample" is a biological sample which is derived from blood, preferably peripheral (or circulating) blood. A blood sample may be, for example, whole blood, plasma or serum.

In preferred embodiment the methods of the herein disclosed invention are performed in vitro method or ex vivo.

In some embodiments of the invention it is preferred that the step of acquiring the sample to be tested from a subject, such as a patient, is excluded from the described methods.

The antigenic protein is preferably a cell surface antigen, and may preferably comprise a transmembrane domain or a trans-membrane anchor. The term "cell surface antigen" refers to a biological molecule that is expressed and targeted to the cellular surface, i.e. the cellular membrane. Although the use of cell surface antigen is preferred to perform the methods of the present invention, also any other antigens that are expressed to be exclusively located in or on the probing cell species may be used. For allowing a binding between the antigenic protein with the candidate antibody species of the invention a probing cell can also be fixed and permeabilized to allow a candidate antibody species to enter the probing cell. Thus, most preferred is that the antigenic protein is not a secreted protein.

The one or more antibody species to be detected with the methods of the invention is a human antibody, and wherein the antibody binding agent is an anti-human antibody. The term "antibody" as used herein includes antibody from a monoclonal or polyclonal source which is produced in response to an antigen, as well as fragments, chimeric forms, altered forms and derivatives of such antibody, as well as chemically and recombinantly produced forms thereof. The term "anti-human antibody" as used herein refers to an antibody which recognizes and binds to human immunoglobulin.

In some embodiments the probing cell species is a cell that does not endogenously express the antigenic protein nor any other protein that could be bound by the one or more antibody species to be detected, preferably, wherein the probing cell species is not a human cell, such as a mouse cell, or alternatively not a mammalian cell, most preferably an invertebrate cell, such as an insect cell. Although the method also works in an isogenic scenario such as detecting a human antibody species by using the herein described methods comprising a human cell as a probing cell species, it is nevertheless a preferred embodiment to use a cell that cannot express the antigenic protein, nor a protein that is closely related to the antigenic protein used in the methods of the present invention. It is advantageous for the methods of the invention to reduce the possibility of unspecific binding of the candidate antibody species with other components expressed in or on the probing cell species. The easiest approach used in context of the invention is to select a probing cell species which is derived from a different organism than the antibody species to be detected. For example, if the antibody species to be detected is a human antibody, it would be preferably to use a probing cell species derived from a non-human cell line, such as a mouse or rat cell.

In order to provide the probing cell species of the invention, an antigenic protein as described above and a detectable label have to be expressed therein. This is preferably achieved by recombinant expression of the antigenic protein and/or detectable label. Therefore it is preferred that in context of the invention the probing cell species comprises a first genetic construct encoding the antigenic protein, and a second genetic construct encoding the second detectable label, or wherein the antigenic protein and the second detectable label are encoded on one genetic construct.

As used herein, the term "genetic construct" refers to the DNA or RNA molecules that comprise a nucleotide sequence, which encodes an antigenic protein or a detectable label. The coding sequence includes initiation and termination signals operably linked to regulatory elements including a promoter and polyadenylation signal capable of directing expression in the probing cell species used for the performance of the method of the invention.

As used herein, the term "expressible form" refers to gene constructs which contain the necessary regulatory elements operable linked to a coding sequence that encodes a detectable label or antigenic protein, such that when present in the cell species, the coding sequence will be expressed.

A "detectable label" in context of the present invention is a detectable marker that can produce a signal that is detectable by visual or instrumental means, e.g., a fluorescent protein, a protein with the incorporation of a radiolabeled amino acid or attachment to a polypeptide of biotinyl moieties that can be detected by marked avidin or streptavidin (e.g., streptavidin containing a fluorescent marker or enzymatic activity that can be detected by optical or colorimetric methods). Examples of labels for polypeptides include, but are not limited to, the following: radioisotopes or radionuclides (e.g., 3H 14C, 35S, 90Y, 99Tc, 111In, 125I, 131I, 177Lu, 166Ho, or 153Sm), chromogens, fluorescent labels (e.g., FITC, rhodamine, lanthanide phosphors), enzymatic labels (e.g., horseradish peroxidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), and magnetic agents (e.g., gadolinium chelates).

Representative examples of labels commonly employed for immunoassays include moieties that produce light, e.g., acridinium compounds, and moieties that produce fluorescence, e.g., fluorescein. A detectable label of the invention may be directly expressed or alternatively coupled to a component that is intended to get detectably labeled for example the antibody binding agent of the invention.

Preferably said first detectable label and second detectable label produce signals that are distinguishable, such as fluorescent proteins producing light signals with different wave lengths.

A fluorescent label refers to a protein that when excited with the necessary wave length is able to fluoresce or produce light. For the purpose of the present invention a fluorescent protein is a protein that when excited with an appropriate wave length results in emission of a light signal that may be detected. In a preferred embodiment the emission spectrum from the fluorescent protein according to the invention is between 445-660 nm, between 550-660 nm and most preferably between 550-660 nm.

Fluorescent proteins when used as labels in context of the invention may be selected from a green fluorescent protein selected from the group of EGFG, AcGFP, TurboGFP, Emerald, Azani Green and ZsGreen, b. blue fluorescent protein selected from the group of EBFP, Sapphire and T-Sapphire, c. cyan fluorescent protein selected from the group of ECFP, mCFP, Cerulean, CyPet, AmCyan1, Midori-Ishi Cyan and mTFPI (Teal), d. yellow fluorescent protein selected from the group of EYFP, Topaz, Venus, mCitrine, Ypet, PhiYFP, ZsYellow1 and mBanana, e. orange and red fluorescent proteins selected from Kusabira Orange, mOrange, dTomato, dTomato-Tandem, DsRed, DsRed2, DsRed-Express (T1), DSRed-Monomer, mTangerine, mStrawberry, AsRed2, mRFP1, Jred, mCherry, HcRed1, mRaspberry, HcRed-Tandem, mPlum and AQ143. The sequences and methods for their detection of the aforementioned fluorescent labels are well known to the person of skill in the art.

In some embodiments of the invention the presence of a signal from the first detectable label and the second detectable label for each probing cell is performed cytometrically or microscopically. As described above, the present disclosure provides cytometric methods for the detection of probing cells. The term "cytometric methods" is used herein to describe flow cytometric methods and/or imaging cytometric methods. Accordingly, "cytometric assay" may refer to a flow cytometric assay and/or imaging cytometric assay, and "cytometer" may refer to a flow cytometer and/or imaging cytometer.

Alternatively the presence of the first and the second detectable label may be analyzed using a fluorescent microscope.

Although the method is in principle applicable for the detection of any antibody in a sample, in certain preferred embodiments the antibody species of the invention is an antibody species specific for a blood group antigen, and wherein the antigenic protein is the corresponding blood group antigen. The term "blood group antigen" is intended to mean any antigen of the ABO system with the A antigen, the B antigen, the A and B antigens expressed simultaneously or the H antigen, of the Rh system with the D, E, e, Cw, and C or c antigens, of the Kell system with the K or k antigen, of the Duffy system (Fya, Fyb), of the Kidd system (Jka, Jkb) system or else of other systems that are less commonly investigated in practice but that also exist, such as MNS, Lewis, etc. Furthermore included under this term are platelet antigens (HPA) and neutrophil antigens (HNA)

In this embodiment the method of the invention may be for use in the detection of a blood group antigen in a sample obtained from a subject, wherein said sample obtained from a subject is the biological sample.

The above described method of the invention comprises the detection of one antibody species in sample. More preferred is however to use the method in the detection of a plurality of distinct candidate antibody species that could be present in the sample. In this aspect for each of the antibody species to be detected, a distinct corresponding probing cell species with the corresponding antigenic protein (which is capable of binding the candidate antibody species) and a distinct detectable label is provided. During step (a) of the disclosed method, the sample is brought into contact with all the probing cell species and the antibody binding agent. Complexes of different antibodies and probing cell species—if they are formed depending on the presence or absence of the plurality of candidate antibody species to be detected—can then be distinguished from another on basis of the second detectable labels used in the probing cell species. Depending on the combination of first and second detectable label observed for a probing cell, one can deduce the presence or absence of the antibody species. Therefore for this embodiment it is detrimental that the first and second or further detectable labels are all distinguishable from one another.

One exemplary embodiment pertains to a method for the detection of any of at least two or more antibody species in a sample, the method comprising:
   a. Contacting a sample suspected to contain any of the two or more antibody species with two or more probing cell species and an antibody binding agent,
      i. wherein the antibody binding agent is coupled to a first detectable label and is capable of binding antibodies, and
      ii. wherein a first probing cell species expresses, or is capable to express, a second detectable label and a first antigenic protein, the first antigenic protein comprising an antigenic portion that is capable of binding, or is capable to be bound by, a first antibody species to be detected; and
      iii. wherein a second probing cell species expresses, or is capable to express, a third detectable label and a second antigenic protein, the second antigenic protein comprising an antigenic portion that is capable of binding, or is capable to be bound by, a second antibody species to be detected; and
   b. Detecting the presence of a signal from the first detectable label, the second detectable label and the third detectable label for each probing cell,
wherein in a probing cell the presence of a signal from the first detectable label and the presence of a signal from the second detectable label indicates the presence of the first antibody species in the sample, and/or wherein in a probing cell the presence of a signal from the first detectable label and the presence of a signal from the third detectable label indicates the presence of the second antibody species in the sample.

The above method may be further expanded by adding probing cell species (iv, v, vi etc.) having respective fourth, fifth, sixth, etc. detectable labels in order to provide a method that is capable to detect three, four, five or more antibody species to be detected. In this case, as also explained above, all the first to fifth or more detectable labels should be distinguishable.

Another aspect of the invention then pertains to an antibody detection system, comprising one or more probing cell species and an antibody binding agent, characterized in that the antibody binding agent is coupled to a first detectable label and is capable of binding antibodies, and each of the one or more probing cell species expresses or is able to express a distinct antigenic protein, wherein said distinct antigenic protein comprises a distinct antigenic portion that can bind to, or is bound by, a distinct antibody species to be detected, and a second detectable label, wherein the second detectable label is different to (i.e. distinguishable from) any other detectable labels of other probing cell species in the system, and wherein a signal of a second detectable label species in the system indicates the presence of the corresponding antigenic protein in the probing cell.

In a preferred embodiment the antibody detection system according to the invention is provided having fluorescent labels as described herein elsewhere as the first and/or second detectable labels.

Corresponding to the afore described method of the invention, also the antibody detection system may in preferred embodiments be expanded for providing an expanded system that is capable of detecting a plurality of antibody species (two, three, four, five to ten, or more). In order to expand the system further probing cell species are included which are similar to the other probing cell species but have distinct specificities to the further antibody species to be detected and further distinct detectable labels (third, fourth, etc), which are preferably distinguishable from any of the other detectable labels in the system.

In this regard an antibody detection system is preferred wherein the system comprises two, three, four, five, ten or more probing cell species, and wherein each probing cell species does not endogenously express any of the antigenic proteins of any of the probing cell species in the system.

The advantages of a method and system for the detection of a plurality of distinct antibody species in a sample is that using the method or system of the invention enables the analysis of the presence of a plurality of antibody species at the same time.

Another aspect of the invention then pertains to a diagnostic kit, comprising the antibody detection system as described herein before. The diagnostic kit of the invention is preferably for use in a method as described herein before.

Another aspect of the invention then pertains to a use of the method, the antibody detection system or diagnostic kit according to the various embodiments and aspects of the invention, in the diagnosis of a clinical status, condition or disease which is characterized by the presence of one or more anti-body species in a biological sample from a subject to be diagnosed. The use is preferably an in vitro or ex vivo use.

The above second problem of the invention is solved in a first aspect by a method for removing an antibody species from a sample, comprising
   a. contacting a sample suspected to contain the antibody species with a trapping cell species under conditions which allow the antibody species to bind to the trapping cell species and to form a trapping cell antibody complex species, and wherein the trapping cell species expresses, or is capable to express, an antigenic protein having an antigenic portion which binds to or can be bound by, the antibody species, and
   b. subsequently, removing the trapping cell antibody complex species from the sample to obtain a purified sample.
   c. optionally, re-probing the trapping cell species with a detectable label allowing detection of antibody bound to the surface of the trapping cell species.

The definition of the term "sample" in this aspect is similar as the definition of sample provided herein above for the other aspects of the invention.

In some embodiments the antibody species and the trapping cell species are derived from different organisms, for example, when the antibody species to be removed is human, the trapping cell species is selected from a non-human species, for example mouse, or vice versa. With this embodiment it is intended to avoid cross reactivities of the trapping cell species with other antibodies that might be present in the sample to be purified.

Alternatively the above method includes that the trapping cell species does not endogenously express the antigenic protein.

In some embodiments removing the trapping cell antibody complex species is performed by centrifugation or filtering and separating the cell free supernatant. How to separate cellular material from liquids is well known in the art. Preferably the method of separation does not harm or destroy the trapping cell species.

In some embodiments the method comprises further:
d. testing the purified sample for the presence of antibodies of the antibody species, wherein in the case of a presence of residual antibodies of the antibody species to be removed, method steps (a) to (b), and optionally (c), are repeated until the purified sample is devoid of any residual antibodies of the antibody species.

For example in some preferred embodiments step (d) comprises a method of detecting antibodies as described herein before, or a conventional antibody screening assay.

Similarly to the above aspects relating to antibody detection, also in this aspect of antibody removal the antibody species to be removed is preferably an antibody binding a blood group antigen, and wherein the sample is a serum sample. For more or more specific examples of such antigens, please see the above disclosure.

Preferably the method is an ex vivo or in vitro method.

Also comprised in further aspects of the invention is an antibody removal system for use in the above method, the system comprising one or more trapping cell species, wherein the trapping cell species expresses, or is capable to express, an antigenic protein having an antigenic portion which binds to or can be bound by, an antibody species to be removed from a sample.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Principle of the novel blood group antibody identification test. Details are provided in the example section.

Figure 2:
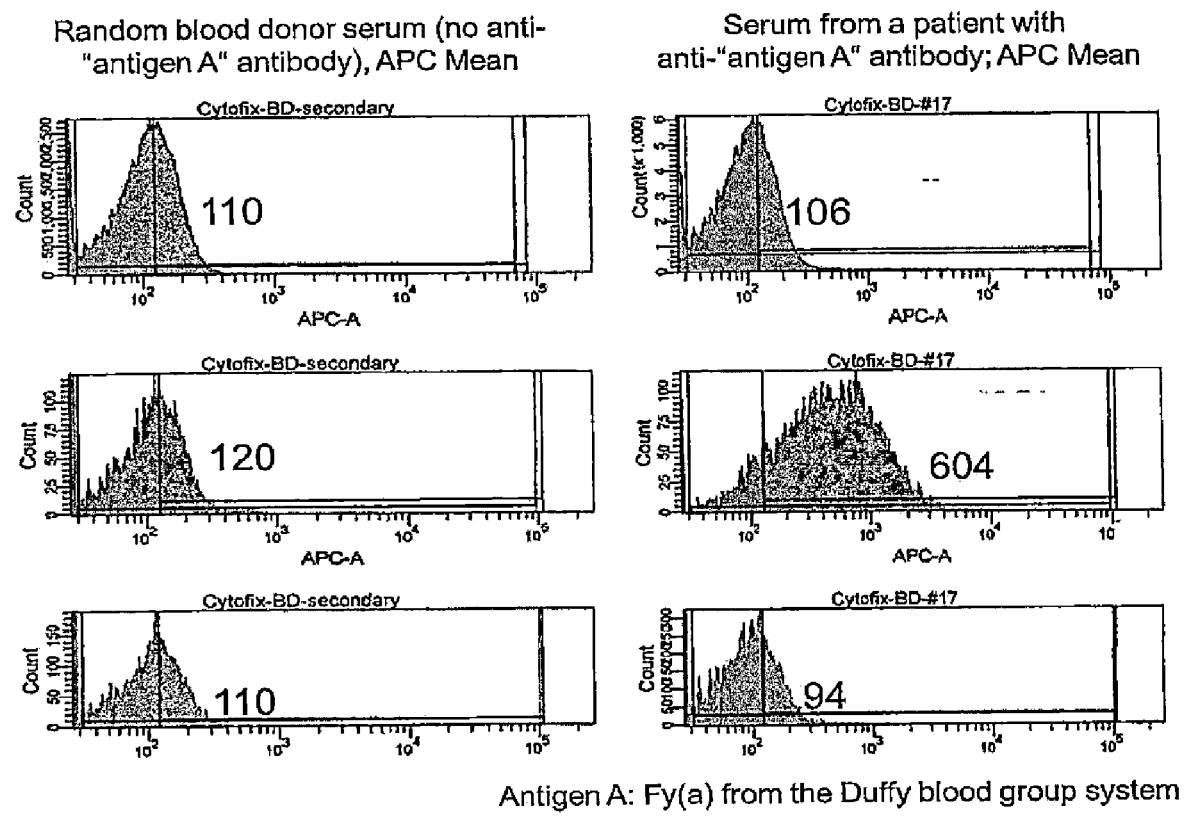

FIG. 2: Representative example, illustrating proof-of-principle of the proposed invention: Cells expressing no antigen and no fluorochrome (negative control) are depicted in blue, cells co-expressing "antigen A" and red fluorescence are shown as dark grey and cells co-expressing "antigen B" and green fluorescence are shown as light grey. Mean APC fluorescence in the left three panels is the same, indicating absence of anti-"antigen A" and anti-"antigen B" antibodies in the tested serum from a random donor. In the right three panels, APC fluorescence is right-shifted (positive) in the middle panel, indicating that the tested serum contains antibody against "antigen A". In this example, "antigen A" is the antigen Fy(a) from the Duffy blood group system, "antigen B" is its counter-antigen, Fy(b). Anti-Fy(a) is a relatively common allo-antibody in poly-transfused patients.

Figure 3:
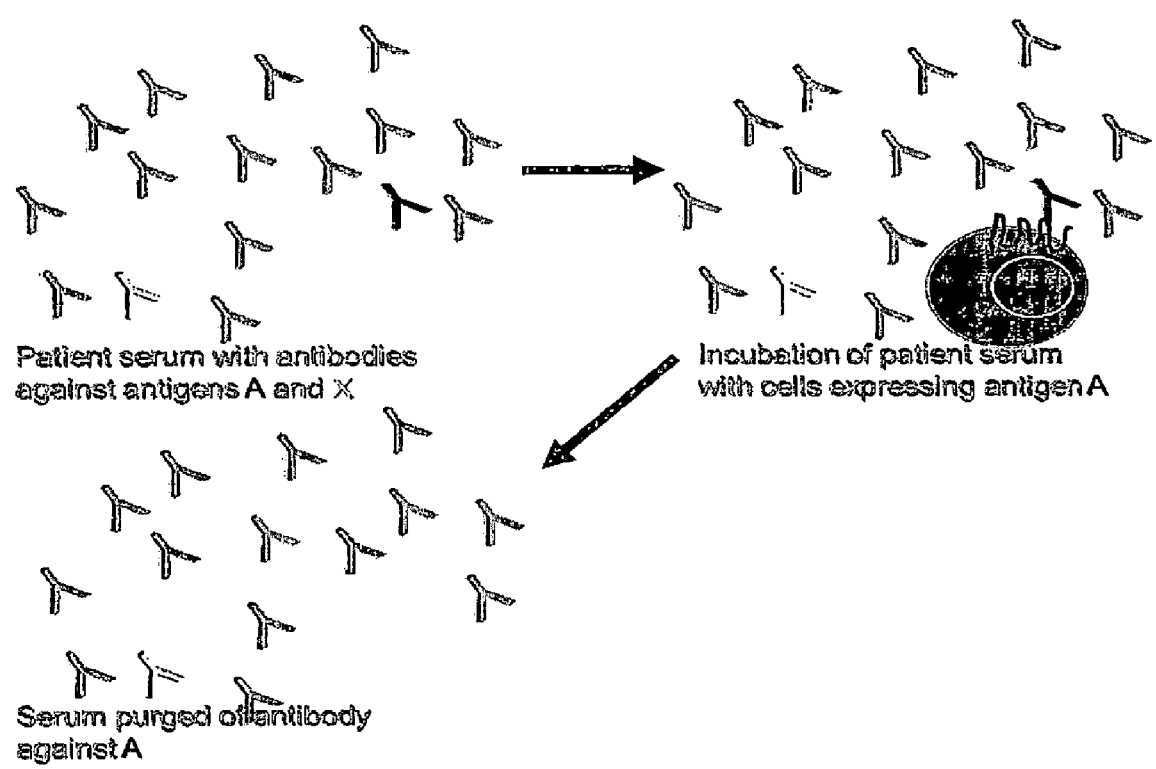

FIG. 3: Principle of absorption method of specific antibody specificities from polyagglutinating sera according to the invention.

Figure 4:
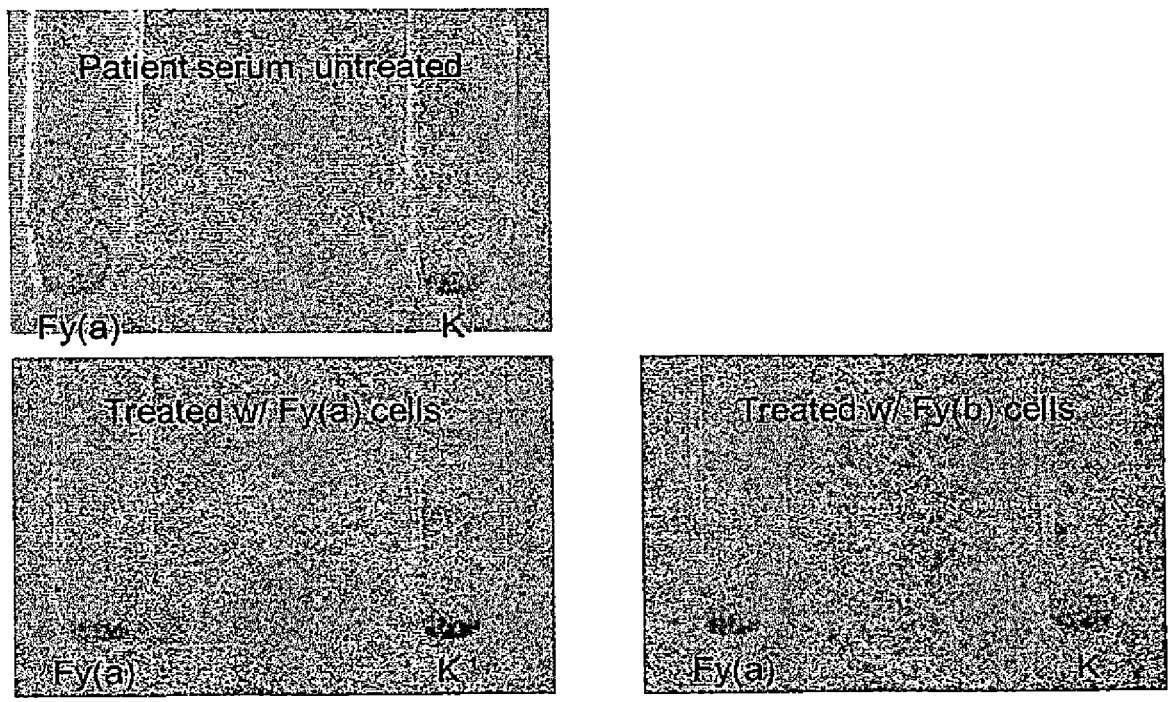

FIG. 4: Representative example, illustrating proof-of-principle of the proposed invention with respect to selective antibody depletion from polyagglutinating serum while qualitatively and quantitatively retaining antibodies against the other specificities.

EXAMPLES

Materials and Methods

MRNAs for blood group antigens are isolated from total RNA isolated from immature hematopoietic blood cells from bone marrow, cord blood or mobilized peripheral blood. cDNA is generated using specific, random or poly-A oligonucleotides. The oligonucleotides may contain restriction sites for insertion into the vector of choice. The blood group antigen encoded by the cDNA is analyzed by sequencing. Either the blood group antigen of choice is primarily isolated, or it may by generated by site-specific mutagenesis. cDNAs may be codon-optimized if so desired. Blood group antigen cDNA is inserted into expression vectors comprising fluorescent reporter genes, expression vectors are amplified, confirmed in identity by full-length sequencing, transduced into target cells. Target cells are immortalized cells continuously growing in cell culture of xenogeneic origin or of human origin but not expressing any blood group antigens.

Cells are transduced, sorted by flow cytometry based on fluorochrome expression, then expanded. Antigen expression is assessed (confirmed) by analysis of DNA (sequencing), mRNA (sequencing), indirect or direct fluorescence by flow cytometric analysis of cells stained with anti-blood group antigen specific antibody, directly or indirectly conjugated to fluorochromes. Re-sorting of cells is considered if the population is not homogeneous with respect to blood group antigen and fluorochrome expression. The highest expressors will be sorted, if applicable.

A cell mix is typically (but not necessarily) generated with equal frequencies of cells expressing each of the different antigens supposed to be represented in the panel. Reasonable antigen combinations would be high-frequency or low-frequency antigens, antigen pairs, antigens against which antibodies are frequently directed, routine panel(s) representing guidelines-mandated antigens, but any other combination is similarly feasible. Specific panels will represent only granulocyte (HNA) antigens or platelet (HPA) antigens; the entire panel of currently known antigens will be represented in each of the panels. Thus diagnostic kits will be generated containing mixed cells representing defined panels of antigens as well as fluorochrome-conjugated secondary antibody and necessary buffers. For antigens frequently observed as obscuring antibody identification, specifically antigens like Rh "D", Rh "e", Kell "k", etc., specific absorption panels will similarly be generated as described above.

Serum with known antibody specificities (during generation of the cells, panels and mixes, as well as during formal validation) or serum from patients suspected of having antibodies against blood group antigens are incubated with the cell mix. Cells are incubated at room temperature or higher (as high as 37° C.) or colder (as low as 4° C.) temperature. Cell-serum mix is washed at least once, subsequently incubated with anti-human IgG-fluorescence coupled, and/or anti-human IgM fluorescence coupled. Thus far, anti-human IgG-APC was used, but any other fluorochrome so long as it does not conflict with that of the individual cells in the cell mix and any other anti-human immunoglobulin can be used. Different anti-human isotype antibodies will be able to determine the isotype of the patient's antibody and hence, its hemolytic potential. Cells are again washed at least once, then subjected to flow cytometry. The additional fluorescence color(s) of the APC-positive cells is assessed. If, for instance, a shift in APC-positivity is observed in cells expressing a red fluorochrome, then serum contained an antibody against the blood group antigen expressed in the red fluorescent cells ("antigen A" in our example, FIGS. 1+2). The serum could contain antibody against several specificities, so that cells of several fluorescence colors could be right-shifted. Serum can be substituted by plasma.

Example 1

Antibody Detection

FIG. 1 illustrates an example test system in accordance with the herein disclosed invention. Using bi- or tri-cistronic vectors, carrying a blood group antigen expression cassette in the first and at least one fluorochrome expression cassette in the second and/or third cloning site, a blood group antigen of choice will be co-expressed with one or more fluorochromes. Transduction of the expression cassettes will be performed with viral or non-viral vectors; instead of bi- or tri-cistronic vectors, concurrent transduction of blood group antigen- and fluorochrome-expressing vectors can be performed alternatively to using multi-cistronic vectors. In this manner, cells expressing "antigen A" as sole blood group antigen will be recognized by their red fluorescence, cells expressing "antigen B" as green, etc. A large panel of fluorochromes which can be combined in all possible combinations, is available allowing for generation of mixed cell populations with an in principle infinite number of different antigens to be tested in a single reaction.

As illustrated in FIG. 1, patient sera containing, among all other IgG specificities anti-"antigen A" antibody will be incubated with the cell mix (containing here, for the sake of the example, only cells expressing no antigen and no fluorochrome (background/negative control), cells co-expressing "antigen A" and red fluorescence and cells co-expressing "antigen B" and green fluorescence). The "antigen A" expressing, red-fluorescing cell will bind the anti-"antigen A" antibody from the serum. A secondary anti-human IgG antibody with APC fluorescence label is next incubated with the cell mix. Only the anti-"antigen A" decorated (red fluorescence-containing) cell will bind the secondary antibody. APC fluorescence will be measured by flow cytometry. Only the red fluorescence-expressing cell population (carrying "antigen A") will be APC-positive.

The results are depicted in FIG. 2. Mean APC fluorescence in the left three panels is the same, indicating absence of anti-"antigen A" and anti-"antigen B" antibodies in the tested serum from a random donor. In the right three panels, APC fluorescence is right-shifted (positive) in the middle panel, indicating that the tested serum contains antibody against "antigen A". In this example, "antigen A" is the antigen Fy(a) from the Duffy blood group system, "antigen B" is its counter-antigen, Fy(b). Anti-Fy(a) is a relatively common allo-antibody in poly-transfused patients.

Example 2

Selective Antibody Absorption

Patient sera may contain more than one antibody specificity against blood group antigens; in the given example as illustrated in FIG. 3, antibodies against blood group antigens A and X. The presence of anti-A may obscure the presence of antibodies against other blood group antigens, or too few test RBCs not negative for antigen A (and thus "reactive" and therefore non-contributory) may stand in the way of excluding the full panel of guidelines-required blood group antigen reactivities. In such a situation, absorption of one specificity may be useful.

Poly-agglutinating patient sera (in this example, containing anti-A and anti-X), therefore, will be incubated with cells expressing a single antigen, in this case antigen A. The residual serum will be recovered and subjected to conventional blood group antibody testing. The expectation is, that RBCs expressing antigen A (but not antigen X) will become non-reactive, while RBCs expressing antigen X will remain reactive. The assay does not make use of the co-expressed fluorescent protein, although incubation of the recovered antigen A expressing cells with anti-IgG-APC and subsequent flow cytometric analysis for confirmation could be entertained.

The results are depicted in FIG. 4. In this example, a patient's serum contained antibodies against two blood group specificities, Fy(a) and K (antigen Kell (KEL1) from the Kell blood group system). Reactivity against Fy(a) homozygous, K-negative test RBCs is shown in the top panel in the left gel column. The subtle positive reaction in the right gel column is directed against Fy(b) homozygous (i.e., Fy(a) negative), Kell heterozygous (Kk) RBCs. Incubation of Fy(a) expressing murine cells (the invention) in the patient serum, followed by precipitation of cells and incubation of the supernatant with the same test RBCs shows the absence of reactivity in the left column (anti-Fy(a) has been completely removed) but the same reaction strength with the cells in the right column. Thus the low-titer anti-K antibody was quantitatively retained. As a second line demonstrating the specificity of the absorption exercise, the same serum was incubated with Fy(b) expressing cells; both antibody specificities were preserved.

The invention claimed is:
1. An in vitro method for the detection of one or more human antibody species in a sample, the method comprising:
   a) contacting a sample suspected to contain the one or more human antibody species with one or more non-human probing cell species and an antibody binding agent,
      i) wherein the antibody binding agent is coupled to a first detectable label and is capable of binding one or more human antibody species, and
      ii) wherein a non-human probing cell of the non-human probing cell species expresses, or is capable to express, a second detectable label and an antigenic protein, the antigenic protein comprising an antigenic portion that is capable of binding, or is capable to be bound by, the antibody of the one or more human antibody species to be detected; and
   b) detecting the presence of a signal from the first detectable label and the second detectable label for the non-human probing cell, wherein the presence of a signal from the first detectable label and the presence of a signal from the second detectable label indicates the presence of the one or more human antibody species in the sample.

2. An in vitro method for the detection of one or more human antibody species in a sample, the method comprising:
   a) contacting a sample suspected to contain the one or more human antibody species with one or more non-human probing cell species and an antibody binding agent,
      i) wherein the antibody binding agent is coupled to a first detectable label and is capable of binding one or more human antibody species, and
      ii) wherein a non-human probing cell of a non-human probing cell species is immobilized at a predetermined location on a solid substrate, and wherein the non-human probing cell expresses, or is capable to express, an antigenic protein, the antigenic protein comprising an antigenic portion that is capable of binding, or is capable to be bound by, the antibody of the one or more human antibody species to be detected; and
   b) detecting the presence of a signal from the first detectable label for the non-human probing cell immobilized on the solid substrate, wherein the presence of a signal from the first detectable label at a predetermined location on the solid substrate indicates the presence of the one or more human antibody species in the sample.

3. The method according to claim 1, wherein the non-human probing cell species is a cell that does not endogenously express the antigenic protein nor any other protein that could be bound by the one or more human antibody species to be detected.

4. The method according to claim 1, wherein said first detectable label and second detectable label produce signals that are distinguishable.

5. The method according to claim 1, wherein said one or more antibody species is an antibody species specific for a blood group antigen, and wherein the antigenic protein is the corresponding blood group antigen.

6. A human antibody detection system, comprising one or more non-human probing cell species and an antibody binding agent, characterized in that
   the antibody binding agent is coupled to a first detectable label and is capable of binding a human antibody species, and
   each of the one or more non-human probing cell species expresses or is able to express a distinct antigenic protein, wherein said distinct antigenic protein comprises a distinct antigenic portion that can bind to, or is bound by, a distinct human antibody species to be detected, and a second detectable label, wherein the second detectable label is distinguishable from any other detectable labels of other non-human probing cell species in the system, and wherein a signal of a second detectable label species in the system indicates the presence of the corresponding antigenic protein in the non-human probing cell.

7. The antibody detection system according to claim 6, wherein the system comprises two or more non-human probing cell species, and wherein each non-human probing cell species does not endogenously express any of the antigenic proteins of any of the non-human probing cell species in the system.

8. A diagnostic kit, comprising the antibody detection system according to claim 6.

9. An in vitro use of the method according to claim 1, in the diagnosis of a disease which is characterized by the presence of one or more human antibody species in a biological sample from a subject to be diagnosed.

10. An in vitro method for removing a human antibody species from a sample, comprising:
   a) contacting a sample suspected to contain the antibody species with a non-human trapping cell species under conditions which allow the antibody species to bind to the trapping cell species and to form a trapping cell antibody complex species, and wherein the trapping cell species expresses, or is capable to express, an antigenic protein having an antigenic portion that binds to or can be bound by, the antibody species, and
   b) subsequently, removing the trapping cell antibody complex species from the sample to obtain a purified sample.

11. The method according to claim 10, wherein the method comprises further:
   c) testing the purified sample for the presence of antibodies of the human antibody species,
   wherein in the case of a presence of residual antibodies of the antibody species to be removed, method steps (a) to (b), and optionally (c), are repeated until the purified sample is devoid of any residual antibodies of the human antibody species.

12. The method according to claim 11, wherein step (c) comprises a method according to claim 1, or a conventional antibody screening assay.

13. The method according to claim 10, wherein the human antibody species to be removed is an antibody binding a blood group antigen, and wherein the sample is a serum sample.

14. The method, according to claim 3, wherein the non-human probing cell species is an insect cell.

15. The method, according to claim 10, wherein the non-human trapping cell species does not endogenously express the antigenic protein.

\* \* \* \* \*